United States Patent [19]

van Gogh et al.

[11] 4,412,056
[45] Oct. 25, 1983

[54] POLYGLYCIDYL ETHERS, THEIR PREPARATION AND USE IN CURABLE COMPOSITIONS

[75] Inventors: Johan van Gogh; Hermanus Grol, both of Amsterdam, Netherlands

[73] Assignee: Shell Oil Company, Houston, Tex.

[21] Appl. No.: 440,647

[22] Filed: Nov. 10, 1982

[30] Foreign Application Priority Data

Dec. 22, 1981 [GB] United Kingdom ............... 8138505

[51] Int. Cl.$^3$ ............................................. C08G 59/24
[52] U.S. Cl. ..................................... 528/112; 528/87; 528/95; 528/121; 528/124; 549/517; 549/560
[58] Field of Search ................. 528/87, 95, 112, 121, 528/124; 549/517, 560

[56] References Cited

U.S. PATENT DOCUMENTS

| 3,305,528 | 2/1967 | Wynstra et al. | 538/95 |
| 3,477,990 | 11/1969 | Dante et al. | 260/47 |
| 3,547,885 | 12/1970 | Dante et al. | 260/47 |
| 3,766,221 | 10/1973 | Becker | 260/348.6 |
| 3,922,253 | 11/1975 | Jerabek et al. | 260/77.5 |

FOREIGN PATENT DOCUMENTS 1556201 11/1979 United Kingdom .

Primary Examiner—Earl A. Nielsen
Attorney, Agent, or Firm—Norris E. Faringer

[57] ABSTRACT

The invention relates to polyglycidyl ethers and provides such compounds based on diphenylol $C_7$ to $C_{13}$ alkanes, and their preparation from the appropriate diphenylol alkanes. The polyglycidyl ethers may be cured with known epoxy resin curing agents and may be used as base materials for the preparation of anionic or cationic aqueous thermosetting paint binders.

The polyglycidyl ethers exhibit good compatibility with aliphatic hydrocarbon solvents.

8 Claims, No Drawings

POLYGLYCIDYL ETHERS, THEIR PREPARATION AND USE IN CURABLE COMPOSITIONS

FIELD OF THE INVENTION

This invention relates to polyglycidyl ethers, their preparation and their use in curable compositions.

BACKGROUND OF THE INVENTION

Polyglycidyl ethers based on 2,2-diphenylolpropane (DPP), also known as 2,2-bis(4-hydroxyphenyl)propane, are well known commercial products. These polyglycidyl ethers, or epoxy resins as they are commonly known, are used on a large scale as the main resinous components in curable or thermosetting compositions, as may be seen from reference to "Handbook of Epoxy Resins", Lee and Neville, McGraw-Hill, New York (1967) and "Uses of Epoxy Resins", Potter, Butterworths, London 1975. These epoxy resins are compounds of general formula:

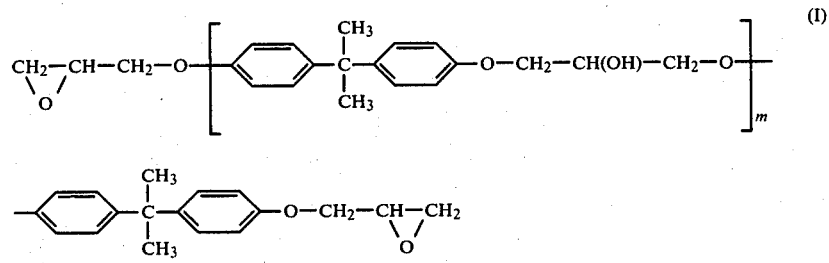

wherein m is a number having an average value from 0 to 12.

A proportion of the glycidyl groups in the above formula may have been replaced by glycol groups, due to the methods of preparation. Compounds of formula I, wherein m is 0-1 are liquid or semi-liquid at room temperature, whereas those wherein m is at least 2 are solids at room temperature.

The glycidyl ethers of DPP have low compatibility with aliphatic hydrocarbons (which are attractive as cheap solvents), and have to be dissolved or diluted with more expensive, polar, solvents, such as ketones or glycol ethers or -esters.

For some purposes, relatively flexible cured products are required. These can be provided by incorporation-reactive flexibilizers, flexibilizing epoxides, and/or flexibilizing curing agents in the products before cure. Apart from price considerations (flexibilizing additives are usually expensive) there is generally a reduction in other useful properties, such as resistance to heat, solvents and/or chemicals.

Liquid epoxy resins based on DPP have the disadvantage that in undiluted form they have relatively high viscosity (commonly of the order of 10 Pa.s or greater at 25° C.). If a resin of lower viscosity is required, the DPP-based resin is diluted with a small proportion of a reactive diluent in the form of a mono- or di-epoxide of low viscosity, such as a glycidyl ether of a monohydric alcohol or a glycol. The inclusion of such reactive diluents tends to impart reduced heat, solvent and/or chemical resistance in the eventual cured products.

U.S. patent application Ser. No. 273,704, filed June 15, 1981, discloses a class of polyglycidyl ethers prepared from a mixture of isomers of 1,1-diphenylol heptane, which are usefully compatible with aliphatic solvents, able to be cured with known epoxy resin curing agents and suitable for use as base materials for the preparation of anionic or cationic aqueous thermosetting paint binders. The low molecular weight polyglycidyl ethers based on the 1,1-diphenylol heptane isomers exhibit low viscosity.

SUMMARY OF THE INVENTION

According to the present invention there is provided a class of polyglycidyl ethers having the general formula:

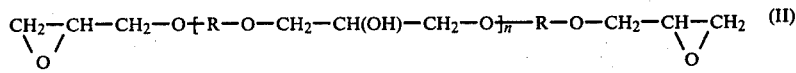

wherein n is a number of from 0 to 12 and R is the hydrocarbon residue of a diphenylol alkane, and wherein from 1 to (n+1) groups R in the above molecule have the formula:

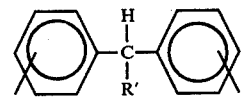

wherein R' is a $C_7$ to $C_{12}$ alkyl group.

DESCRIPTION OF THE PREFERRED EMBODIMENT

The polyglycidyl ethers of formula II noted above may be prepared in accordance with the invention by a process which comprises reacting a diphenylol alkane with epichlorohydrin or with a polyepoxide, the diphenylol alkane being a compound of general formula:

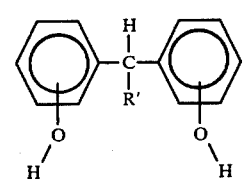

wherein R' is a $C_7$ to $C_{12}$ alkyl group.

Such processes may result in a small proportion of the terminal epoxy groups in the ethers of formula II being replaced by glycol groups. However, a polyglycidyl ether in accordance with the invention contains on average more than one epoxy group per molecule.

The residues of formula III, and the diphenylol alkanes of formula IV from which they are derived, may exist in a variety of isomeric forms, para,para'-, ortho,- para- and ortho,ortho'-residues. In polyglycidyl ethers of the invention, conveniently para,para'- and ortho,-para'-residues of formula III are present in a weight ratio from 90:10 to 40:60, preferably from 80:20 to 40:60.

It has been found that when n in formula II has an average value from 0 to 1 the polyglycidyl ethers derived from diphenylol alkanes of formula IV wherein R' is an n-alkyl group are "liquid" resins having the lowest viscosities. Accordingly, preferred polyglycidyl ethers of formula II are those wherein at least 50%, preferably at least 65%, of the R' groups are n-alkyl groups, the remainder being alpha-methylalkyl groups. Such "liquid" epoxy resins may be prepared in high yields by reaction of the appropriate diphenylol alkane of formula IV with epichlorohydrin, or dichlorohydrin, and an alkali metal hydroxide, if desired in the presence of catalysts or solvents.

The diphenylol alkanes of formula IV may conveniently be prepared by reaction of the appropriate aldehyde of formula R'CHO with a molar excess of phenol in the presence of hydrochloric acid, if desired in the presence of mercapto co-catalysts, at moderate temperatures; the excess of phenol and the catalyst can be removed after the reaction, for example by distillation. The product, the residue, is a mixture of diphenylol alkane isomers, containing mainly p,p'-isomer and o,p'-isomer (in a weight ratio of from 80:20 to 40:60), and may contain up to 10% by weight of higher condensates (trisphenol derivatives). The weight ratio p,p'-isomer to o,p'-isomer is usually from 65:35 to 55:45, and the amount of o,o'-isomer is low, for example up to about 6%.

At, or slightly above, ambient temperatures the resulting mixtures of diphenylol alkane isomers are typically sticky, tar-like compounds which may readily be diluted with solvent or reagent required for conversion into glycidyl ethers. For the latter reaction there is no need to separate the isomers, or to enrich the content of one of the isomers, although separation or enrichment may be effected in known manner, if desired. Thus, the mixtures of diphenylol alkane isomers may be diluted for example with epichlorohydrin and/or alcohols such as methanol, ethanol, n-propanol, isopropanol, n-butanol, isobutanol and s-butanol.

Aldehydes of formula R'CHO may be prepared by known hydroformylation reaction from the appropriate alpha-olefins. Typically, aldehydes obtained from linear alpha-monoolefins contain about 70%w of straight-chain isomer and about 30%w of the alpha-methyl isomer. Preferably the group R' contains an even number of carbon atoms since the corresponding linear alpha-olefins are particularly readily obtainable commercial products. Advantageously R' contains 8 carbon atoms.

In general, the diphenylol alkanes of formula IV described above may be converted into polyglycidyl ethers of the invention by methods analogous to those known for the preparation of diglycidyl ethers of 2,2-bis(4-hydroxyphenyl)propane.

Thus the "liquid" polyglycidyl ethers, wherein n has an average value from 0 to 1 may conveniently be prepared by reacting the diphenylol alkane with a molar excess of epichlorohydrin, if desired first in a pre-reaction in the presence of a catalyst for the promotion of chlorohydrin ether formation, whereafter the equivalent amount, or, preferably, an excess, of alkali metal hydroxide is added in one or more stages for dehydrohalogenation.

So-called "solid" polyglycidyl ethers (wherein n in the above formula II is at least 2) may be prepared by reacting the diphenylol alkane in aqueous medium with less epichlorohydrin and with alkali metal hydroxide in a single stage.

Polyglycidyl ethers of formula II, wherein n is at least 2 may also be prepared by reaction of an underdose of a diphenylol alkane with a diglycidyl ether of a diphenylol alkane in the presence of a small amount of a catalyst, for example, a phosphine, a tertiary amine, a quaternary ammonium salt, or a quaternary phosphonium salt, for example as described in U.S. Pat. No. 3,547,881 and U.S. Pat. No. 3,447,990. Various types of polyglycidyl ethers according to the invention may be prepared by this method. Thus, a diphenylol alkane of formula IV may be reacted with a diglycidyl ether of the same diphenylol alkane, or with a diglycidyl ether of 2,2-bis(4-hydroxyphenyl)propane, or further 2,2-bis(4-hydroxyphenyl)propane may be reacted with a diglycidyl ether of a diphenylol alkane of formula IV. The resulting polyglycidyl ether will then contain from 1 to (n+1) residues of formula III per molecule, the remaining hydrocarbon residues R being derived from the 2,2-diphenylol propane.

Polyglycidyl ethers according to the invention may be modified by reaction with all types of modifying agents known for the known epoxy resins, for example with fatty acid to prepare epoxy resin esters, with amines (excess) to prepare soluble epoxy resin/amine adducts, with dicarboxylic acids (underdose) to prepare epoxy resins having a dicarboxylic acid ester group in the chain.

The polyglycidyl ethers according to the invention may be used in particular as base materials for the preparation of anionic or cationic aqueous thermosetting binders for paints, for application by electrodeposition. Some of such methods have been described in U.S. Pat. No. 3,922,253 and U.K. Pat. No. 1,556,201.

Polyglycidyl ethers according to the invention may be converted to hard resinous materials by mixing and reacting with known epoxy resin curing agents. Useful curing agents include amino compounds, in particular those having at least two amino hydrogen atoms per molecule. Examples are aliphatic polyamines, aromatic polyamines, soluble adducts thereof with mono-epoxides and/or di-epoxides, amino amides derived from aliphatic polyamines and carboxylic acids, heterocyclic polyamines. Cure with amino compounds may be accelerated by phenols or monocarboxylic acids. Other useful curing agents include polycarboxylic acids and polycarboxylic acid anhydrides; the cure may be accelerated by small amounts of catalysts, such as tertiary amines, for example benzyldimethylamine, or 2,4,6-tris(dimethylaminomethyl)phenol, stannous slats, and others. Further examples of curing agents are polyisocyanates, phenolic resins, and aminoplast resins.

Solvents, diluents, extenders (coal tar, asphaltic bitumen), fillers and pigments may also be added, depending on the intended use. Polyglycidyl ethers according to the invention wherein n has a value from 0 to 1 can be used as main binder components in coating compositions, in particular for solventless or high solids coating compositions, or for use in civil engineering, for example for coverage of floors, road surfaces, bridge decks, as adhesive, or for casting, moulding, laminating, for example for electrical applications. Further uses to be mentioned are as binders in grouts, as resinous components in tooling operations, and for cable jointing compositions. In flooring compositions these polyglycidyl ethers allow a very high filler loading.

Polyglycidyl ethers according to the invention wherein n is greater than 1 may find a use in coatings, laminates, or adhesives.

The use of polyglycidyl ethers according to the invention provides in general an improved solubility in aliphatic hydrocarbon solvents and very good pigment wetting, and after cure an excellent adhesion on conventional substrates, improved flexibility, and very good chemical resistance.

Polyglycidyl ethers of the invention may, if desired, be blended with other epoxy resins, e.g., with the known diglycidyl ethers of 2,2-bis(4-hydroxyphenyl)-propane.

The invention will be illustrated by the following illustrative examples wherein parts and percentages are by weight unless otherwise noted.

EXAMPLES 1 TO 4

Preparation of diphenylol alkanes

Phenol (705 g, 7.5 moles) was melted and saturated with gaseous HCl at 50° C. with vigorous stirring over 15 minutes (HCl content about 1%w). The appropriate aldehyde (0.5 mole) was added to the resulting solution of HCl in phenol over 1 minute and the reaction mixture was stirred for thirty minutes during which the temperature rose to 60°–65° C.

Water, HCl and excess phenol were removed by vacuum distillation, initially at 15 mm Hg up to 80° C. to remove the bulk of the phenol, followed by vacuum steam distillation (75 mm Hg, 120° C., about 45 minutes) and finally under nitrogen (40 mm Hg, maximum temperature 140° C.).

The resulting curde 1,1-diphenylol alkanes were sticky, tar-like compounds which crystallized partly on storage at ambient temperature. Yield data and results of analyses for phenolic hydroxyl content are given in Table I. The 2-ethyl-hexanal was obtained ex BASF, W. Germany. The $C_9$ to $C_{13}$ aldehydes were obtained by known hydroformylation reaction from the corresponding linear $C_8$ to $C_{12}$ alpha-monoolefins and therefore were mixtures of isomers, about 70%w being straight-chain isomer and the remaining about 30%w being alpha-methyl isomer.

TABLE I

| Example | Starting Material | Yield of 1,1-diphenylol alkane (g) | | Phenolic hydroxyl content (mmol/kg) | |
|---|---|---|---|---|---|
| | | Theoretical (0.5 mol) | Found | Theoretical | Found |
| 1 | 2-ethylhexanal | 149 | 143 | 6711 | 6690 |
| 2 | $C_9$—aldehyde | 156 | 151 | 6410 | 6200 |
| 3 | $C_{11}$—aldehyde | 170 | 163 | 5882 | 5780 |
| 4 | $C_{13}$—aldehyde | 184 | 175 | 5435 | 5320 |

High performance liquid chromatography (HPLC) showed the ratio of para,para'-1,1-diphenylol-2-ethylhexane to ortho,para'-1,1-diphenylol-2-ethylhexane to be 56:27. Para,para'- and ortho,para'-isomers are also present in the products based on $C_9$ to $C_{13}$ aldehydes, but the chromatograms are complicated by the presence of the alpha-methyl isomers.

EXAMPLES 5 TO 8

Preparation of liquid epoxy resins

The appropriate 1,1-diphenylol alkane from Examples 1 to 4 (0.33 mole) was dissolved in a mixture of epichlorohydrin (370 g, 4 moles), i-propanol (216 g, 3.6 moles) and water (54 g, 3 moles) in a 1 liter reactor. The solution was heated to 45° C., and aqueous sodium hydroxide (133 g of a 20%w solution, 0.66 mole NaOH) was added gradually over 40 minutes with stirring during which the temperature rose to 50° C., after which the reaction mixture was stirred for a further 20 minutes at 60° C. On cessation of stirring the reaction mixture separated into two phases. The lower, aqueous phase, a weakly alkaline sodium chloride solution, was drained off. To the organic phase was added a further quantity of aqueous sodium hydroxide (44 g of the 20%w solution; 0.22 mole NaOH) and the mixture was stirred vigorously for 5 minutes at 60° C. On cessation of stirring the mixture separated into two phases. The lower, aqueous phase was drained off and the organic phase was washed consecutively with water (160 ml), 2%w aqueous $NaH_2PO_4$ (160 ml) and water (160 ml). Isopropanol and excess epichlorohydrin were distilled off, final traces being removed by vacuum distillation and steam distillation as in Examples 1 to 4. The procedure was repeated using 2,2-diphenylol propane (DPP) as a control in place of the 1,1-diphenylol alkane.

The diglycidyl ethers obtained were liquid epoxy resins having a yield data and properties as listed in Table II.

TABLE II

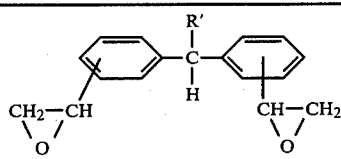

| Example | | 5 | 6 | 7 | 8 | control |
|---|---|---|---|---|---|---|
| Starting material | | Ex. 1 | Ex. 2 | Ex. 3 | Ex. 4 | DPP |
| R' | | 1-ethyl-pentyl | $C_8$ alkyl | $C_{10}$ alkyl | $C_{12}$ alkyl | |
| Yield (g) | Theoretical | 136.5 | 141 | 150.5 | 160.0 | 113 |
| | Found | 130.5 | 134.5 | 143.5 | 152.5 | 107 |
| Epoxy group concentration (mmol/kg) | Theoretical | 4880 | 4720 | 4420 | 4170 | 5880 |
| | Found | 4525 | 4386 | 4050 | 3830 | 5555 |
| Alpha-glycol | | 13 | 10 | 10 | 10 | 20 |

TABLE II-continued

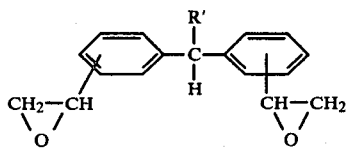

| Example | 5 | 6 | 7 | 8 | control |
|---|---|---|---|---|---|
| Starting material | Ex. 1 | Ex. 2 | Ex. 3 | Ex. 4 | DPP |
| content (mmol/kg) | | | | | |
| Phenolic OH—content (mmol/kg) | 40 | 20 | 30 | 20 | 10 |
| Saponifiable chloride content (mg/kg) | 1300 | 1100 | 1900 | 1300 | 300 |
| Total Cl—content (mg/kg) | 2150 | 2200 | 2700 | 2200 | 1260 |
| Viscosity (25° C.) (Pa.S) | 65 | 3.8 | 3.0 | 2.4 | 8.4 |

EXAMPLES 9 TO 11

Solventless coating formulations for ambient temperature cure

The epoxy resins of Examples 6 to 8 were tested in solvent-free ambient temperature curing formulations, in comparison with an equivalent formulation based on the commercially available epoxy resin "EPIKOTE 828" (a glycidyl polyether of 2,2-bis(4-hydroxyphenyl)-propane having an average molecular weight of 380-390 and an epoxy equivalent weight of about 180-190). The composition of the formulations are given in Table III.

TABLE III

| Example Epoxy resin | 9 Ex. 6 | 10 Ex. 7 | 11 Ex. 8 | Comparison "EPIKOTE 828" |
|---|---|---|---|---|
| Amount of resin (parts by weight) | 100 | 100 | 100 | 100 |
| red iron oxide (parts by weight) | 15 | 15 | 15 | 15 |
| asbestine (parts by weight) | 15 | 15 | 15 | 15 |
| microtalc (parts by weight) | 10 | 10 | 10 | 10 |
| Diethylene triamine (curing agent) (parts by weight) | 9.2 | 8.5 | 8.0 | 11.1 |
| Gel time (minutes) of unpigmented resin/curing agent blend (Tecam method according to BS 2782 method III D) | 124 | 126 | 141 | 47 |

The formulations were applied by brush to degreased, shot-blasted cold-rolled mild steel panels to a film thickness of about 80 microns. The resulting films were cured for 14 days at 23° C. before testing of mechanical properties and chemical resistance. Results of tests on the cured films are given in Table IV, in which assessments for chemical resistance are given according to the ASTM blister rating.

TABLE IV

| Example | 9 | 10 | 11 | Comparison |
|---|---|---|---|---|
| Hardness (Buchholz) | 87 | 83 | 74 | 100 |
| Erichsen slow penetration (mm) | 7.5 | 6.5 | >8 | 1 |
| Ford impact resistance (cm · kg) direct | 16 | 21 | 34 | 16 |
| Cross-hatch adhesion (Gitterschnitt) | Gt = 0 | Gt = 0 | Gt = 0 | Gt = 0 |
| Chemical resistance to: | | | | |
| distilled water, 70° C., 3 weeks | 10 | 10 | 10 | 10 |
| 5% w caustic, 20° C. 3 weeks | 8 M | 8 MD | 10 | 10 |
| 5% w sulphuric acid, 20° C., 3 weeks | >2 MD | 8 F | 8 − 2 D | >2 D |
| 5% formic acid, 20° C., 1 day | 6 D | 6 D | 2 M | TLA |
| Salt spray 200 hours | 3 + 8 M | 3 + 6 MD | 3 + 8 M | 3 + 8 F |
| 500 hours | 5 + 6 D | 4 + 6 D | 6 + 6 D | 4 + 8 M |
| Humidity 500 hours | very few rust in score | few rust spots in score | very few rust spots in score | rust spots in score |

For salt spray and humidity resistance the panels were scratched on one side to bare metal. The rating given for salt spray is width of underrust from the scratch (mm) plus ASTM blister rating.

EXAMPLES 12 TO 16

Preparation of liquid epoxy resins

Further samples of liquid epoxy resins based on 2-ethylhexanal, n-nonanal and the $C_9$ to $C_{13}$-aldehydes used in Examples 2 to 4 were prepared by a similar process to that described in Examples 5 to 8. The properties of the resins in comparison with "EPIKOTE 828" are given in Table V.

TABLE V

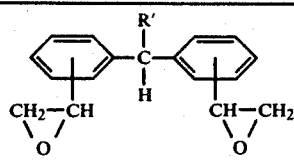

| Example | | 12 | 13 | 14 | 15 | 16 | "EPIKOTE 828" |
|---|---|---|---|---|---|---|---|
| Starting aldehyde | | as Ex. 1 | n-nonanal | as Ex. 2 | as Ex. 3 | as Ex. 4 | |
| R' | | 1-ethyl-pentyl | n-octyl | $C_8$—alkyl | $C_{10}$—alkyl | $C_{12}$—alkyl | |
| Epoxy group conc. (mmol/kg) | Theoretical | 4480 | 4720 | 4720 | 4420 | 4170 | 5880 |
| | Found | 4630 | 4350 | 4420 | 4160 | 3880 | 5350 |
| Viscosity (25° C.) (Pa.s) | | 72.0 | 2.1 | 3.2 | 2.9 | 2.3 | 9.6 |
| Density (25° C.) (g · cm$^3$) | | 1.08 | 1.07 | 1.07 | 1.05 | 1.03 | 1.16 |
| Surface tension (22° C.) (dyne/cm$^2$) | | 42.0 | 39.5 | 39.0 | 36.5 | 37.0 | 50.5 |
| % n-hexane tolerated (23° C.) | | 17.4 | 25.1 | 25.9 | 51.2 | ∞ | <2.5 |

The % n-hexane tolerated is the %w of n-hexane in a resin/hexane mixture at which the mixture just becomes turbid and provides a general indication of miscibility of the resins with aliphatic solvents. It is to be noted that the resin of Example 16 is miscible in all proportions with n-hexane and "EPIKOTE 828" cannot be diluted with n-hexane to any significant extent.

The high viscosities of the resins of Examples 12 and 5 render them unsuitable for use in solventless coating formulations, although they may be used as a base material in the preparation of solid resins. The increased viscosity appears to be associated with the branching at the alpha-carbon atom of R', which conclusion is reinforced by a comparison of Examples 13 and 14. Example 14, which has higher viscosity than Example 13, contains about 30% of alpha-methyl isomer whereas R' in Example 13 is a straight-chain alkyl group.

EXAMPLES 17 TO 19

Unpigmented solventless coatings

The epoxy resins of Examples 14 to 16 were tested in unpigmented solvent-free ambient temperature curing formulations, in comparison with an equivalent formulation based on "EPIKOTE 828". The formulations consisted of the epoxy resins blended with the calculated stoichiometric amount of a commercially available curing agent, "EPIKURE 153" (a modified aromatic polyamine curing agent which contains 4,4'-diaminodiphenylmethane and which has basic nitrogen content of 6.6 to 7.2% by weight, viscosity at 25° C. of 4.0 to 6.5 Pa.s, refractive index $n^{25}$=1.587-1.592, density at 25° C. of 1.09 g/ml, flash point of 117° C., vapor pressure at 20° C. less than 0.01 mm Hg and at 80° C. less than 1.5 mm Hg).

The formulations could be applied by brush. Film properties were assessed on films of about 150 microns thickness applied to glass plate (hardness only) and to grit-blasted mild steel panels by means of a doctor blade. The films were cured for 14 days at 23° C. Results are given in Table VI.

TABLE VI

| Epoxy resin | 14 | 15 | 16 | "EPI-KOTE 828" |
|---|---|---|---|---|
| Amount of resin (parts by weight) | 100 | 100 | 100 | 100 |
| Amount of curing agent (parts by weight) | 48.6 | 45.8 | 42.6 | 60.0 |
| Hardness of glass (Buchholz) | 80 | 77 | 74 | 111 |
| Hardness on steel (Buchholz) | 87 | 83 | 80 | 111 |
| Erichsen slow penetration (mm) (after 7 day cure) | 9.3 | >9.4 | >7** | 0.9 |
| Erichsen impact resistance (mm) (after 7 day cure) | >6* | 5-6 | >6* | <1 |
| Chemical resistance to: | | | | |
| MEK rubs | 30 | 30 | 30 | 20 |
| 5% w sulfuric acid | + | + | + | + |
| 5% w sodium hydroxide | + | + | + | + |
| Xylene | ± | — | — | + |

MEK = methyl ethyl ketone;
+ = good resistance,
± = fair resistance,
— = poor resistance,
— — = very poor resistance;
*maximum of test,
**measurement stopped at 7 mm.

EXAMPLE 20

Preparation of liquid epoxy resin based on n-nonanal 1,1-diphenylol nonane was prepared from n-nonanal by a similar process to that of Examples 1 to 4 in 93% yield and had phenolic hydroxyl content 5900 mmol/kg (theoretical 6410 mmol/kg). HPLC revealed that the ratio of para,para'- to ortho,para'-isomers was about 50:35 (analysis: p,p'-isomer 49.13%, o,p'-isomer 35.78%, o,o'-isomer 5.61%, trisphenol derivative 8.50%, unknown 0.94%, phenol 0.04%).

Some of this 1,1-diphenylol nonane was used to prepare a liquid epoxy resin in the form of the diglycidyl ether of 1,1-diphenylol nonane by a similar process to that described in Examples 5 to 8. The yield was 95%w and the liquid epoxy resin had epoxy group concentration 4310 mmol/kg (theoretical 4720 mmol/kg), alpha-glycol concentration 20 mmol/kg, phenolic OH-content 30 mmol/kg, saponifiable chloride content 500 mg/kg, and viscosity 2.0 Pa.s at 25° C.

EXAMPLE 21

Solventless coating formulation for ambient temperature cure

The epoxy resin of Example 20 was tested on a solvent-free ambient temperature curing formulation in comparison with an equivalent formulation based on "EPIKOTE 828", using diethylene triamine as curing agent.

The formulations were applied by brush to degreased, shot-blasted cold-rolled mild steel panels to a film thickness of about 80 microns. The resulting films were cured for 7 days at 23° C. before testing. The compositions of the formulations and the test results are given in Table VII, in which assessments of chemical resistance are given according to the ASTM blister rating.

TABLE VII

|  | Example 20 | "EPIKOTE 828" |
|---|---|---|
| Amount of resin (parts by weight) | 100 | 100 |
| Amount of curing agent (parts by weight) | 8.9 | 10.3 |
| red iron oxide (parts by weight) | 15 | 15 |
| microtalc (parts by weight) | 10 | 10 |
| Hardness (Buchholz) | 80 | 100 |
| Erichsen slow penetration (mm) | 4 | 0.5 |
| Gardner impact resistance (mm) (direct) | 12 | 4 |
| Cross-hatch adhesion (Gitterschnitt) | Gt = 0 | Gt = 0 |
| Chemical resistance to: |  |  |
| distilled water, 70° C., 20 weeks | 10 | 10 |
| 5% w caustic, 20° C., 8 weeks | 10 | 10 |
| 5% w caustic, 20° C., 20 weeks | 4 F | 6 VF |
| 5% w sulphuric acid, 20° C., 12 weeks | 8 M | 4 D |
| 5% w formic acid, 20° C. 4 days | 8 MD | TLA |

TLA = total loss of adhesion.

EXAMPLES 22 TO 24

Preparation of fusion resins

Fusion resins were prepared from the 1,1-diphenylol nonane described in Example 20 above and "EPIKOTE 828" by the following general process. "EPIKOTE 828" (3.5 epoxy equivalents) and 1,1-diphenylol nonane (calculated quantity) were heated to 110° C. and catalyst solution (0.2 ml of a 50%w solution of tetramethylammonium chloride) was added. The temperature rose to 165° C. over 75 minutes and the reaction mixture was maintained for 2½ hours. More catalyst solution (0.1 ml) was added, and after a further hour at 165° C. a third quantity of catalyst solution (0.1 ml) was added and the temperature was maintained for another ½ hour to bring the reaction to completion, before cooling to ambient temperature. Three resins were prepared and the quantities of 1,1-diphenylol nonane used were those required (based on measured phenolic hydroxy content of 5900 mmol/kg of the 1,1-diphenylol nonane) to give theoretical epoxy group contents of 2170, 540 and 350 mmol/kg, which fall within the epoxy group content ranges of the commercially available solid diphenylolpropane resins "EPIKOTE 1001", "EPIKOTE 1007" and "EPIKOTE 1009" respectively ("EPIKOTE" is a registered Trade Mark).

The properties of the resins are given in the following Table VIII, data for "EPIKOTE 1009" being included for comparative purposes.

TABLE VIII

| Example | 22 | 23 | 24 | "EPIKOTE 1009" |
|---|---|---|---|---|
| Epoxy group Theoretical (mmol/kg) | 2170 | 540 | 350 |  |
| concentration Found (mmol/kg) | 2070 | 530 | 345 | 323 |
| Alpha-glycol content | 50 | 40 | 40 | 240 |
| Phenolic OH—content | 50 | 190 | 210 | 26 |
| Viscosity of 40% w solution in butyldiglycol at (25° C.) (Pa.s) | — | 0.8 | 1.3 | 5.9 |

These resins were all solid at room temperature, but when a sample of the resin of Example 22 was crushed, the resulting pieces gradually flowed into an amorphous mass.

Solutions of the resin of Example 22 above 25%w in xylene remained clear after 6 weeks' storage at 0° C. The viscosity of a 70%w solution of the resin of Example 22 in xylene at 25° C. rose from an initial value of 1023 centistokes (compare 2511 centistokes for "EPIKOTE 1001") to 1161 centistokes after 8 days storage at 0° C. (compare 3269 centistokes for "EPIKOTE 1001").

For surface coating applications where the presence of aromatic hydrocarbon solvents is undesirable (e.g., can coatings), expensive solvents such as ketones and alkyl glycols and diglycols and their acetates are commonly used with solid resins such as "EPIKOTE 1007" or "EPIKOTE 1009". Experiments have shown that solutions of the resins of Examples 22 to 24 in such solvents (e.g., methyl ethyl ketone, methyl isobutyl ketone, ethyl glycol, ethyl glycol acetate) will tolerate dilution with larger quantities of cheaper solvents such as ethanol, 1-propanol, n-butanol, methylisobutylcarbinol and the blend of $C_5$ to $C_8$ paraffins and cycloparaffins having a distillation range 144°–165° C. and sold by the Royal Dutch/Shell group of companies under the designation "SBP 140/165", than will equivalent solutions of "EPIKOTE 1001", "EPIKOTE 1007" and "EPIKOTE 1009" respectively.

EXAMPLE 25

Solvent-based primer formulation for ambient temperature cure

The epoxy resin of Example 22 was tested in a coating formulation in comparison with an equivalent formulation based on "EPIKOTE 1001" as resin component. The constitutions of the formulations are given in Table IX, in which all quantities are parts by weight.

TABLE IX

| Epoxy resin | Example 22 | "EPIKOTE 1001" |
|---|---|---|
| Amount of 75% w solution of resin in xylene | 150 | 150 |
| xylene | 137 | 30 |
| n-butanol (NBA) | — | 22.5 |
| methyl ethyl ketone (MEK) | — | 22.5 |
| zinc phosphate (pigment) | 28.0 | 28.0 |
| red iron oxide (pigment) | 154.5 | 154.5 |
| microtalc (filler) | 30.5 | 30.5 |
| Xylene/NBA/MEK (in weight ratio 6:2:2) | — | 62.0 |

Immediately before application as paints there was added to each of the formulations as curing agent a 75%w solution in xylene of a polyaminoamide curing agent derived from dimerized fatty acids (commercially available as "VERSAMID 115") ("VERSAMID" is a Trade Mark) in a weight ratio epoxy resin:curing agent of 100:40 (both calculated on solids content).

The formulations were then immediately sprayed onto degreased, shot-blasted, cold-rolled mild steel panels to a film thickness of about 25 microns. The resulting films were cured for 7 days at 23° C. before testing. Test results are given in Table X, assessments of chemical resistance being given according to the ASTM blister rating.

TABLE X

| Epoxy resin | Example 22 | "EPIKOTE 1001" |
|---|---|---|
| Hardness (Buchholz) | 95 | 100 |
| (Koenig) | 147 | 111 |
| Erichsen slow penetration (mm) | >8 | >8 |
| Gardner impact resistance (mm) (direct) | 30 | 30 |
| Cross-hatch adhesion (Gitterschnitt) | Gt = 0 | Gt = 0 |
| Mandrel bend (conical) | pass | pass |
| Chemical resistance to: | | |
| distilled water, 70° C., 8 weeks | 10 | 10 |
| 5% w caustic, 20° C., 8 weeks | 4 VF | 8 MD |
| 5% w sulphuric acid, 20° C., | 8 VF | 2 VF |
| xylene, 20° C., 8 weeks | 10 | 10 |
| methyl isobutyl ketone, 20° C., 8 weeks | 10 | 10 |
| salt spray 240 hours | 2 + 10 | 1 + 8 F |
| 500 hours | 2 + 10 | 5 + 8 MD |
| 750 hours | 2 + 6 F | 5 + 6 MD |
| 1500 hours | 2 + 4 F | 5 + 4 MD |
| humidity 1500 hours | 10 | 10 |

Salt spray and humidity test procedures and ratings are as defined in Examples 9 to 11.

What is claimed is:

1. A polyglycidyl ether having the general formula:

CH$_2$—CH—CH$_2$—O $\underset{\diagdown \diagup}{O}$ (R—O—CH$_2$—CH(OH)—CH$_2$—O)$_n$ —R—O—CH$_2$—CH—CH$_2$ $\underset{\diagdown \diagup}{O}$ wherein n is a number of from 0 to 12 and R is the hydrocarbon residue of a diphenylol alkane from 1 to (n+1) groups R in the above molecule have the formula:

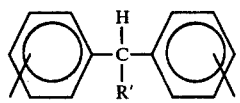

wherein R' is a C$_7$ to C$_{12}$ alkyl group.

2. The polyglycidyl ether of claim 1 wherein para,-para'- and ortho,para'-residues are present in a weight ratio from 90:10 to 40:60.

3. The polyglycidyl ether of claim 2 wherein the weight ratio is from 80:20 to 40:60.

4. The polyglycidyl ether of claim 1 wherein at least 50% of the R' groups are n-alkyl groups, the remainder being alpha-methylalkyl groups.

5. The polyglycidyl ether of claim 1 wherein the group R' contains an even number of carbon atoms.

6. A process for the preparation of the polyglycidyl ether of claim 1 wherein a diphenylol alkane is reacted with epichlorohydrin or with a polyepoxide, said diphenylol alkane having the general formula:

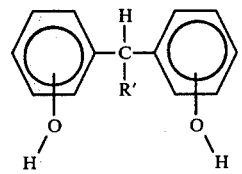

wherein R' is a C$_7$ to C$_{12}$ alkyl group.

7. A process for curing the polyglycidyl ether of claim 1 which comprises mixing and reacting the polyglycidyl ether with a curing amount of an epoxy resin curing agent.

8. The process according to claim 7 wherein the curing agent is selected from the group consisting of an amino compound, a polycarboxylic acid, and a polycarboxylic acid anhydride.

* * * * *